United States Patent [19]

Slaugh

[11] 3,996,256
[45] Dec. 7, 1976

[54] METHANATION CATALYST
[75] Inventor: Lynn H. Slaugh, Houston, Tex.
[73] Assignee: Shell Oil Company, Houston, Tex.
[22] Filed: Dec. 22, 1975
[21] Appl. No.: 642,871
[52] U.S. Cl. .................. 260/449 M; 48/197 FM; 252/458
[51] Int. Cl.$^2$ .................. C07C 1/16; C07C 1/04
[58] Field of Search .................. 260/449 M
[56] References Cited
UNITED STATES PATENTS
3,941,819  3/1976  Vannice et al. .................. 260/449 M OTHER PUBLICATIONS
Wencke, Chem. Abs. (1960) 17022 C.

Primary Examiner—Howard T. Mars

[57] ABSTRACT

The reaction of hydrogen and carbon oxides (carbon monoxide and carbon dioxide) to form methane at temperatures above 300° C is promoted by carrying out the reaction in the presence of a catalyst containing molybdenum disilicide.

3 Claims, No Drawings

METHANATION CATALYST

BACKGROUND OF THE INVENTION

Catalytic methanation is a well-known reaction which is widely employed in the chemical and energy providing industries. Probably its most widespread current and potential application is in the treatment of the gaseous effluent from the gasification or partial oxidation of carbonaceous fuels with oxygen and/or water, e.g., steam-hydrocarbon reforming and partial combustion of liquid and solid carbonaceous fuels, to produce a hydrogen-rich gas for chemical synthesis, e.g., ammonia manufacture, or petroleum refining, e.g., catalytic hydrocracking and hydrogenation, or to form a methane-rich gas having high BTU value and low CO content for use in residential and industrial heating or power generation. In the former case, the gasification or partial oxidation effluent, which typically contains substantial quantities of $H_2$, CO, $CO_2$ and $H_2O$ as well as $N_2$ in cases where air is used as the oxidant source, is generally subject to a process known as the carbon-monoxide shift-conversion reaction prior to catalytic methanation. In this case, the CO-shift reaction converts a substantial quantity of the CO present to $H_2$ and $CO_2$ by reaction with $H_2O$ in the presence of a catalyst and the primary purpose of catalytic methanation is to remove small quantities of CO which remain in the hydrogen-rich product gas by conversion to methane in order to avoid poisoning of downstream processing catalysts. In the latter case, i.e., conversion of partial oxidation effluent gas to methane-rich gas, the gasification or partial oxidation effluent gas is subject to CO-shift to obtain the appropriate ratio of $H_2$ to CO (usually 3 to 1) and the CO-shift product gas is then subject to catalytic methanation for conversion of carbon oxides and hydrogen contained therein to methane. In either case, the CO-shift effluent gas is typically subject to an intermediate processing step to remove sulfurous materials in cases where a sulfur-containing carbonaceous fuel feedstock is employed since all commercially used methanation catalysts are highly sensitive to poisoning by sulfur compounds.

Because of the increasing demand for a high BTU, clean gas as an energy source in the United States and the acknowledged decreasing and finite nature of natural gas reserves in the United States as well as happenings on the world scene which make energy self-sufficiency desirable or even essential, there has been a dramatic increase in interest in the manufacture of a clean, high BTU gas energy source which will meet pipeline standards by synthetic means from alternative carbonaceous resources such as coal or heavy hydrocarbons. Many of the more attractive synthetic approaches which have been proposed are based on gasification or partial combustion of the carbonaceous material, and, as indicated above, include catalytic methanation as part of the integrated process scheme to upgrade the BTU value of the product gas to a level acceptable for pipeline gas applications. CO and $H_2$ have heating values of about 300 BTU/ft$^3$ whereas pipeline natural gas has a value near 1000 BTU/ft$^3$. While a number of metallic species are known to be active and selective methanation catalysts including, inter alia, nickel, ruthenium, cobalt and iron, their application to the manufacture of high BTU or pipeline gas has been less than satisfactory for several reasons. In the first place, methanation reactions with these catalyst systems generally must be limited to temperatures below 400° C to avoid sintering and deactivation of the catalyst and the highly exothermic nature of the methanation reaction itself provides severe operational difficulties in controlling catalyst temperature in a fixed or fluidized bed at these levels when the CO concentration of the feed gas is in the range required for methane-rich gas manufacture. Further, the methanation reaction itself, is considered to be a combination of several reactions including the primary reaction (1)

$$3 H_2 + CO \rightarrow CH_4 + H_2O \quad (1)$$

and secondary reactions (2) and (3)

$$2 H_2 + 2CO \rightarrow CH_4 + CO_2 \quad (2)$$

$$4 H_2 + CO_2 \rightarrow CH_4 + 2H_2O \quad (3)$$

whose thermodynamic equilibria are such that the equilibrium yield of methane is adversely effected at high temperatures, i.e., above 500° C. Reaction (2) is a combination of reaction (1) and the water gas shift reaction (4).

$$CO + H_2O \rightarrow CO_2 + H_2 \quad (4)$$

Thus, with conventional catalyst systems, methanations have been limited to the lowest temperatures consistent with acceptable catalyst activity in part, because of catalyst instability at high temperatures, the highly exothermic nature of the methanation reaction and the inability to effect an equilibrium shift towards methane at high temperatures under practical circumstances. A good review of previous efforts in catalytic methanation and the problems associated therewith can be found in G. A. Mill et al, "Catalytic Methanation", *Catalysis Reviews*, 8 (2), 159–210 (1973).

Accordingly, it would be desirable if an active catalyst system for methanation at temperatures above 400° C could be developed which would minimize operational problems associated with high temperature operation of the solid, particulate catalysts of the prior art. It would also be very beneficial if the catalyst system employed were sulfur resistant. In that case, it would be possible to eliminate, or reduce the severity of, the intermediate desulfurization step typically employed before the methanation reaction.

THE PRIOR ART

It is known that the carbides of various transition metals, including titanium, vanadium, chromium, manganese, zirconium, columbian, molydenum, masurium, hafnium, tantalum, tungsten, rhenium, thorium, protoactinium and uranium, are useful in producing liquid and gaseous hydrocarbons by the catalytic reduction of carbon monoxide with hydrogen. See U.S. Pat. No. 2,539,414. Likewise, the borides and nitrides of the above-noted transition metals have also been shown to be useful in producing gaseous and liquid hydrocarbons from carbon monoxide and hydrogen. See U.S. Pat. No. 2,507,510 and U.S. Pat. No. 2,531,420, respectively. However, the above-noted catalysts are not particularly sulfur resistant.

A novel methanation catalyst has now been found that not only is active in promoting the reaction of carbon oxides and hydrogen, but also is relatively sulfur resistant.

SUMMARY OF THE INVENTION

The present invention is a continuous process for the production of methane from a gaseous reactant mixture containing gases selected from the group comprising hydrogen, carbon monoxide, and carbon dioxide which process comprises contacting said gaseous reactant mixture in the reaction zone maintained at temperatures above about 300° C with a catalyst containing molybdenum disilicide ($MoSi_2$).

DETAILED DESCRIPTION OF THE INVENTION

The Catalyst

Molybdenum disilicide ($MoSi_2$) has been found to be an effective catalyst in the catalytic reduction of carbon oxides and hydrogen to methane. The molybdenum disilicide may be prepared by any suitable process, and preferably is prepared by direct reaction of the elements heated in vacuo or in a protective atmosphere. Various possible methods to produce molybdenum disilicide are disclosed in Aronsson et al, *Borides, Silicides and Phosphides*, John Wiley & Sons, New York (1965) pages 1–9. Preferably, the molybdenum disilicide is employed as a relatively pure catalyst. However, it is within the scope of the invention that the molybdenum disilicide be supported on conventional supports or that the molybdenum disilicide be incorporated with other inert or catalytically reactive compounds.

Preferably, the molybdenum disilicide will be in the form of particles having a surface area of between about 0.1 and about 15 $m^2/g$.

In addition to being an active methanation catalyst, molybdenum disilicide is also relatively sulfur resistant. For example, while molybdenum carbides, borides, and nitrides are also active for methanation, the carbides, borides and nitrides of molydenum become totally inactive and are poisoned by the presence of 3000 to 4000 ppm of $H_2S$ in the gaseous reactant feed. Molybdenum disilicide, on the other hand, still retained a conversion rate of over 2% after 1.5 hours of $H_2S$ treatment (3,000 to 4,000 ppm $H_2S$ in feed stream). Further, once the introduction of the $H_2S$ had been stopped, the molybdenum disilicide regained about half of its original activity in only about six hours. This sulfur resistance is a significant advantage over other methanation catalysts.

The Methanation Reaction

The gaseous reactant feed to the catalytic methanation process of the invention must contain at least some measurable amount of hydrogen and carbon oxides (carbon dioxide and/or carbon monoxide). Preferably, the reactant feed mixture to methanation contains both hydrogen and carbon monoxide at an $H_2:CO$ mole ratio of 2:1 with $H_2:CO$ reactant mole ratios of 3:1 or more being most preferred. Gaseous reactant feed mixtures which can be suitably methanated with catalyst compositions of the instant invention typically contain 10 to 99.9% $H_2$, 0.1 to 50% CO, 0 to 20% $CO_2$, 0 to 70% $H_2O$, 0 to 25% $CH_4$ and 0 to 70% $N_2$. Such gaseous reactant feed mixtures are quite suitably obtained from conventional partial oxidation or gasification of carbonaceous fuels such as, inter alia, natural gas or normally gaseous hydrocarbons, e.g., $C_{2-4}$ saturated and olefinic hydrocarbons; heavier hydrocarbon fractions including gasoline, kerosene, naphtha, distillates, gas oils and residual oils; solid or semi-solid fuels including coal, oil shale, partial combustion soot and bituminous residues from petroleum refining. Typically, the partial oxidation or gasification effluent gas will be subject to a conventional CO-shift reaction to adjust the hydrogen to carbon monoxide mole ratio and an optional particulate removal step, e.g., one or more cyclone separators, prior to methanation according to the invention. However, at least the intermediate CO-shift step is not essential to the preparation of a suitable gaseous feedstock for use in the invention since conversion of reactants to methane will still be effected to the extent that the stoichiometry of the reaction can be satisfied.

One of the applications of the catalytic methanation process of the instant invention is in the upgrading of methane-rich gas derived from the partial oxidation or gasification of coal. Several coal gasification processes employing non-catalytic gasifiers in which coal is converted to a crude product gas containing principally $CH_4$, $H_2$, CO, $H_2O$ and $CO_2$ by high temperature reaction with steam and oxygen are quite well known, e.g., the Lurgi process, the Koppers-Totzek process, etc., and need not be detailed herein. A catalytic steam gasification process for conversion of coal to methane-rich gas by reaction with steam in the presence of certain alkali carbonate catalysts at about 600°–750° C is described in U.S. Pat. No. 3,686,240 to Aldridge et al. In general, all of these coal gasification processes are endothermic in the gasification stage and produce a suitable gas feed mixture for methanation according to the instant invention.

Procedurally, the methanation process of the instant invention can be suitably effected by any conventional technique for intimately contacting a gaseous reactant feed with a catalyst. Such techniques include batch or continuous procedures wherein the gas is introduced into the vapor phase of a reaction chamber or autoclave containing the catalyst and the catalyst is agitated into contact with the gas mixture. In the case of a batch reaction according to this procedure, the product gas is merely withdrawn at the end of the reaction (measured by time and/or pressure drop) whereas in the case of a continuous reaction the size of the reaction chamber and catalyst to gas ratios in the reaction chamber are selected to allow sufficient gas-catalyst contact prior to continuous withdrawal of product gas at some point in the vapor phase remote from the reactant feed port. Alternatively, the gas phase can be passed into countercurrent contact with the catalyst phase in a vertically-oriented contacting column. In any case, the methanation reaction zone is maintained at temperatures above about 300° C while the gaseous reactant feed mixture is in contact with the catalyst. Preferably, the methanation reaction according to this invention is effected at temperatures between about 300° and 700° C and most preferably between about 500° and 650° C. The pressures employed in the methanation reaction according to the invention generally range between one atmosphere and 100 atmosphere pressure and preferably between about 50 to about 80 atmospheres.

The reaction or contact time is not considered critical to the operation of the methanation process of the instant invention. Accordingly, the reaction time should be at least 0.01 second with reaction time of about 1 second being a reasonable maximum for practical operation. Preferably, the reaction time ranges from about 0.02 to about 0.5 second. In this regard, the ratio of volume of reactant feed gas to catalyst in continuous processes employing the methanation catalyst of the invention may suitably range from about 900 to about 10,000 cubic centimeters of gas per cubic centimeter of catalyst per hour (gas measured at STP).

The invention is further illustrated by means of the following Illustrative Embodiments and Comparative Examples. Note that the embodiments and examples are given for purposes of illustration only and that the invention is not to be regarded as limited to any of the specific conditions or reactants recited therein.

In Illustrative Embodiment I, a gaseous reactant mixture comprising hydrogen and carbon monoxide in a mole ratio of about 3:1 is contacted in a reaction zone with a molybdenum disilicide catalyst. The molybdenum disilicide catalyst, in the form of solid particles having a surface area of about 0.05 m²/g, was loaded in a vertical contacting vessel with inert supports above and below the catalyst to prevent entrainment of the catalyst. The pressure was atmospheric and the temperature and gas hourly space velocity (GHSV) were varied as shown in Table I below. The activity of the catalyst is measured by conversion of CO to $CH_4$ and is expressed by the formula:

$$\text{conversion} = \frac{\text{moles } CH_4 \text{ in product}}{\text{moles } CO \text{ and } CH_4 \text{ in product}} \times 100.$$

The minor conversion of CO to $CO_2$ is not taken into account. The results are presented below in Table I.

Table I

| Run No. | Catalyst (grams) | Catalyst (cubic centimeters) | $H_2$/CO Feed (GHSV) | Temp. (° C) | Conversion (%) |
|---|---|---|---|---|---|
| 1 | 6.5 | 3 | 600 | 500 | 20 |
| 2 | 6.5 | 3 | 900 | 600 | 20 |

COMPARATIVE EXAMPLE I

Various other transition metal silicides have been examined for methanation activity, and have not been found to be useful. The catalysts below were tested under similar conditions to the $MoSi_2$ of Illustrative Embodiment I (3:1 $H_2$/CO mixture, 1 atmosphere pressure, similar reactor configuration). The results are presented below in Table II.

Table II

| Run No. | Catalyst (type) | Catalyst (grams) | Catalyst (cubic centimeters) | $H_2$/CO Feed (GHSV) | Temp. (° C) | Conversion (%) |
|---|---|---|---|---|---|---|
| 1 | ZrSi | 5 | 3 | 900 | 500 | None |
| 2 | ZrSi | 5 | 3 | 900 | 600 | None |
| 3 | $VSi_2$ | 6 | 3 | 900 | 600 | Trace |
| 4 | MoSi | 7 | 3 | 900 | 600 | Trace |
| 5 | $Cr_3Si_2$ | 8 | 3 | 900 | 600 | Trace |
| 6 | $Cr_3Si_2$ | 8 | 3 | 900 | 700 | Trace |
| 7 | $WSi_2$ | 13 | 3 | 900 | 600 | Trace |

What is claimed is:
1. A process for the production of methane from a gaseous reactant mixture containing hydrogen, carbon monoxide and/or carbon dioxide which comprises contacting said gaseous mixture in a reaction zone maintained at a temperature between about 300° C and about 700° C with a catalyst comprising molybdenum disilicide.

2. The process according to claim 1 wherein the gaseous reactant mixture contains hydrogen and carbon monoxide at an $H_2$:CO mole ratio of at least 2:1.

3. The process according to claim 2 wherein a gas hourly space velocity of between about 900 and about 10,000 standard cubic centimeters of gaseous reactant mixture per cubic centimeter of catalyst per hour is maintained.

* * * * *